United States Patent
Barry

Patent Number: 5,383,921
Date of Patent: Jan. 24, 1995

[54] THERAPEUTIC MUFF

[76] Inventor: Shirley K. Barry, 4972 Mt. Casas Dr., San Diego, Calif. 92117

[21] Appl. No.: 283,545

[22] Filed: Aug. 1, 1994

[51] Int. Cl.⁶ .................................................. A61F 7/00
[52] U.S. Cl. ..................................... 607/114; 426/113; 607/111; 383/901
[58] Field of Search ................. 426/113; 607/108–112, 607/114; 383/901; 62/530

[56] References Cited

U.S. PATENT DOCUMENTS 5,300,104  4/1994  Gaudreault et al. ................. 607/114
5,300,105  4/1994  Owens ................................... 607/114

Primary Examiner—Lee S. Cohen
Assistant Examiner—Robert L. Nasser, Jr.
Attorney, Agent, or Firm—Lewis E. Massie

[57] ABSTRACT

A therapeutic tubular muff containing temperature maintaining material for applying heat or cold to the body extremities including the hands, the wrists, the arms, the ankles and legs of the user. The muff is constructed of flexible material, including fleece material for the internal surface, and denim for the exterior surface. The muff is preheated in a microwave or cooled in a refrigerator before using.

1 Claim, 1 Drawing Sheet

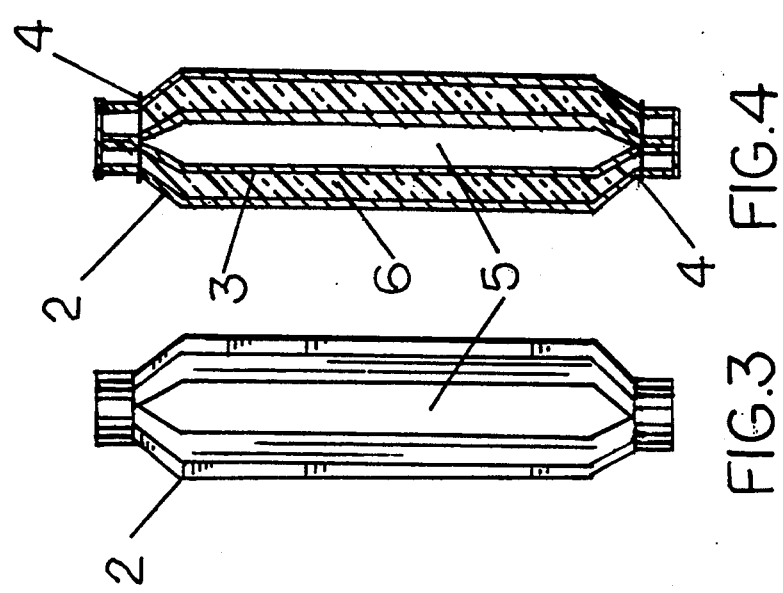
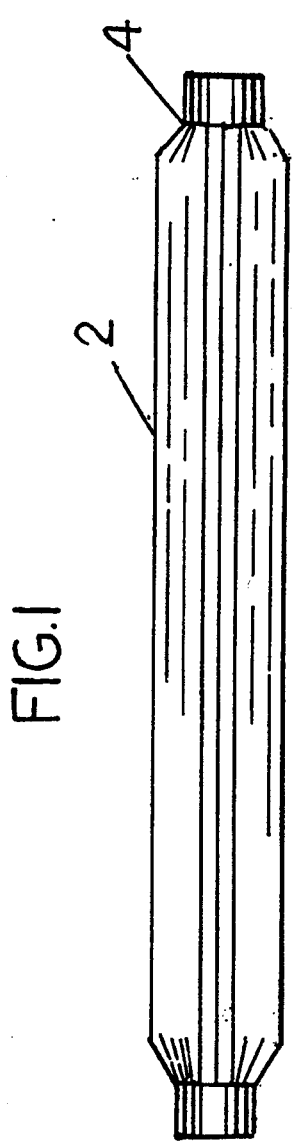
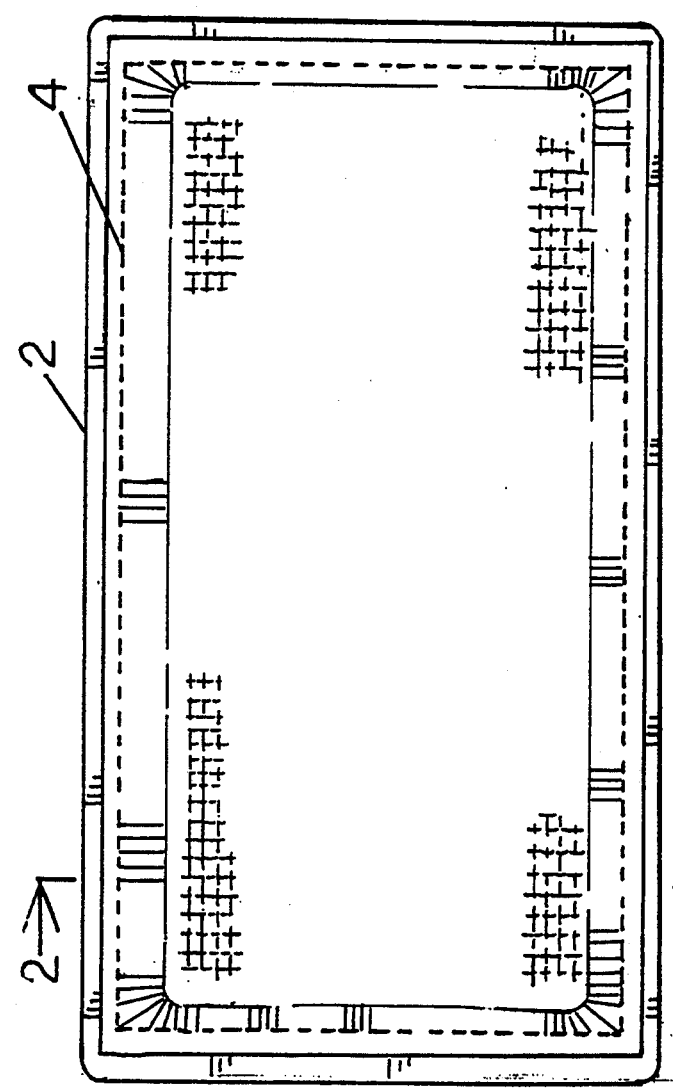

THERAPEUTIC MUFF

BACKGROUND OF THE INVENTION

1. Field of the Invention

Ice packs and hot water bottles are old in the art. Therapeutic use thereof is to apply heat or cold to the user for the reduction of pain and to expedite the healing of injuries and infections or the like.

It is therefore a principal object of this invention to provide a therapeutic muff containing a heating or cooling material, into which a body part such as the hands, wrist, arms, or legs can be inserted.

2. Description of the Related Art

The difficulty in treating the hands, wrists and arms lies in keeping the hot or cold reservoirs in contact with that portion of the body. U.S. Pat. No. 5,265,669 issued to Mark Schneider on Nov. 30, 1939 describes a heat transfer device in the form of a bandanna-like neck band having a main body of flexible fabric material and a pocket lengthwise for receiving an elongated heat transfer element in the form of a multi-cellular reusable coolant pouch therein. U.S. Pat. No. 4,887,326 issued to O'Brien on Dec. 19, 1989 describes a sub-occipital pillow for applying heat and/or cold treatments to the neck and suboccipital areas having a crescent shape and filled with a gel pack which may either cooled in a refrigerated or heated in a microwave oven.

SUMMARY OF THE INVENTION

This invention relates to a device in the form of a muff into which the hands, wrists, arms or legs of the user can be inserted and heat or cold applied to the selected area.

The muff comprises an elongated flexible tubular member the inside diameter of the tube being sufficient to enclose the clasped folded hands of the user. The outer surface of the tubular member being of a denim material and the inner surface being a fleece material. The space between the outer surface and the inner surface filled with a temperature retaining material comprising wheat, cinnamon and cloves. In a device used in close proximity with the body an important consideration is the aroma or odor of the device which can be accentuated by repeated heating and cooling. The inclusion of cinnamon and cloves in the temperature retaining material provides a pleasant aroma in the instant invention.

BRIEF DESCRIPTION OF THE DRAWINGS

FIG. 1 is a top view of the muff;

FIG. 2 is a front view of the muff;

FIG. 3 is a right and view of the muff;

FIG. 4 is a sectional view through 2—2 of FIG. 2.

DETAILED DESCRIPTION OF THE PREFERRED EMBODIMENTS

Referring to FIG. 2 and 4 the tubular muff 2 is shown with the outer front and back denim cover 2 sewn 4 along the top and bottom edges to the inner front and back fleece linear 3 forming a tubular member. The space 6 between the outer and inner liners filled with a temperature retaining medium comprising a ratio of 2 lbs dry wheat, one-half stick of cinnamon and approximately 16 cloves.

The sectional view of FIG. 4 shows the front denim cover 2, the temperature retaining medium 6, the inner liner 3, sewn along the top and bottom edges 4 to the back inside linear and the back outside cover forming the expandable longitudinal opening 5 for insertion of the hands or body parts.

The muff can be used as a soothing heat body pack or as a pliable cold pack. When used as a heat source the muff is heated in a microwave oven for a period of approximately one and one-half minutes or when used for cooling it is placed into a plastic bag and placed into a refrigerator freezer for a period of approximately four hours.

The muff can also be used for back, shoulder, or to slide on arm through for the elbow, wrist, or other parts of the arm. The muff also can be applied to knees, ankles, and legs.

I claim:

1. A therapeutic muff made from two longitudinal tubular segments of flexible material comprising:
   (a) a first tubular segment made of a flexible fleece material having first and second ends;
   (b) said first segment having an inside diameter of approximately six inches and a length of approximately twelve inches;
   (c) a second tubular segment of denim material having first and second ends and an outside diameter of approximately eight inches and a length of approximately twelve inches;
   (d) wherein the first segment is located within the second segment with the respective first and second ends of the first and second tubular segments fastened together to define a circumferential space therebetween;
   (e) said circumferential space being filled with a temperature retaining material comprising a mixture of two pounds of dry wheat, one stick of cinnamon, and twelve cloves.

* * * * *